US007659225B2

(12) United States Patent
Chen et al.

(10) Patent No.: US 7,659,225 B2
(45) Date of Patent: *Feb. 9, 2010

(54) PRECIOUS METAL CATALYST FOR DEBENZYLATION

(75) Inventors: Jian Ping Chen, Hudson, OH (US); Charles R. Penquite, Erie, PA (US); Deepak S. Thakur, Solon, OH (US)

(73) Assignee: BASF Catalysts LLC, Florham Park, NJ (US)

( * ) Notice: Subject to any disclaimer, the term of this patent is extended or adjusted under 35 U.S.C. 154(b) by 628 days.

This patent is subject to a terminal disclaimer.

(21) Appl. No.: 11/144,496

(22) Filed: Jun. 3, 2005

(65) Prior Publication Data

US 2005/0221976 A1 Oct. 6, 2005

Related U.S. Application Data

(63) Continuation-in-part of application No. 09/954,235, filed on Sep. 17, 2001, now Pat. No. 6,992,037.

(51) Int. Cl.
*B01J 21/18* (2006.01)
*B01J 23/00* (2006.01)
*B01J 27/00* (2006.01)
*B01J 27/185* (2006.01)
*C01B 31/08* (2006.01)
*A01N 25/00* (2006.01)

(52) U.S. Cl. .................. 502/182; 502/185; 502/208; 502/213; 502/423; 424/405

(58) Field of Classification Search ............... 502/182, 502/185, 208, 213, 423; 424/405
See application file for complete search history.

(56) References Cited

U.S. PATENT DOCUMENTS

| | | | |
|---|---|---|---|
| 2,409,494 A | 10/1946 | Keating | |
| 2,556,616 A | 6/1951 | Ellis | |
| 2,611,750 A | 9/1952 | White | |
| 3,084,394 A | 4/1963 | Bickerdike et al. | |
| 3,109,712 A | 11/1963 | Redfern | |
| 3,162,607 A | 12/1964 | Burbidge et al. | |
| 3,171,720 A | 3/1965 | Shea, Jr. et al. | |
| 3,198,714 A | 8/1965 | Johnson et al. | |
| 3,235,346 A | 2/1966 | Hucke | |
| 3,288,475 A | 11/1966 | Benoit | |
| 3,310,611 A | 3/1967 | Zocher | |
| 3,342,555 A | 9/1967 | McMillan | |
| 3,345,440 A | 10/1967 | Googin et al. | |
| 3,348,967 A | 10/1967 | Hucke | |
| 3,352,788 A | 11/1967 | Conlisk | |
| 3,387,940 A | 6/1968 | McHenry et al. | |
| 3,446,593 A | 5/1969 | Mostssd | |
| 3,446,865 A | 5/1969 | Roth et al. | |
| 3,544,502 A | 12/1970 | Boyer et al. | |
| 3,565,980 A | 2/1971 | Otani | |
| 3,574,548 A | 4/1971 | Sands et al. | |
| 3,608,170 A | 9/1971 | Larson et al. | |
| 3,626,042 A | 12/1971 | Appleby et al. | |
| 3,628,984 A | 12/1971 | Ishlkawa et al. | |
| 3,634,569 A | 1/1972 | Emanuelson et al. | |
| 3,635,676 A | 1/1972 | Sands | |
| 3,657,166 A | 4/1972 | Caldwell | |
| 3,663,171 A | 5/1972 | Granger | |
| 3,775,078 A | 11/1973 | Elmer et al. | |
| 3,859,421 A | 1/1975 | Hucke | |
| 3,964,933 A | 6/1976 | Fung et al. | |
| 4,029,567 A | 6/1977 | Farnand et al. | |
| 4,031,137 A | 6/1977 | Schmitt, Jr. et al. ..... | 260/559 AT |
| 4,052,336 A * | 10/1977 | van Montfoort et al. ..... | 502/185 |
| 4,061,596 A | 12/1977 | Matsushita et al. | |
| 4,076,873 A | 2/1978 | Shea | |
| 4,082,694 A | 4/1978 | Wennerberg et al. | |
| 4,090,978 A | 5/1978 | Welsh et al. | |
| 4,206,078 A | 6/1980 | Ohorodnik et al. | |
| 4,263,268 A | 4/1981 | Knox et al. | |

(Continued)

FOREIGN PATENT DOCUMENTS

| | | |
|---|---|---|
| EP | 1232789 | 8/2002 |
| WO | WO 0121306 | 3/2001 |
| WO | 03024592 | 3/2003 |

OTHER PUBLICATIONS

Bernotas, Ronald C., et al. "The Use of Pearlman's Catalyst for Selective N-Debenzylation in the Presence of Benzyl Ethers," Synthetic Communications, 20(8), 1209-1212 1990.

(Continued)

*Primary Examiner*—Patricia L Hailey
(74) *Attorney, Agent, or Firm*—Raymond F. Keller

(57) ABSTRACT

Disclosed is a catalyst composite containing a metal catalyst and a specifically defined carbon support containing a carbonaceous material. For example, the carbon support may have a total pore surface area of about 800 $m^2/g$ or more and about 2,000 $m^2/g$ or less where about 20% or less of the total pore surface area is micro pore surface area. Alternatively the carbon support may have a total pore volume of at least about 0.75 cc/g where about 15% or less of the total pore volume is micro pore volume. Alternatively, the carbon support may have a phosphorus content of about 0.75% by weight or less. Also disclosed are methods of making and using the catalyst composite.

20 Claims, No Drawings

U.S. PATENT DOCUMENTS

| | | | |
|---|---|---|---|
| 4,269,737 A | 5/1981 | Grenoble et al. | |
| 4,329,260 A | 5/1982 | Lester et al. | |
| 4,416,804 A | 11/1983 | Antos et al. | 502/213 |
| 4,431,820 A | 2/1984 | Wierenga | |
| 4,500,541 A | 2/1985 | Hausberg et al. | |
| 4,532,227 A | 7/1985 | Suggitt | 502/180 |
| 4,595,765 A * | 6/1986 | Murphy | 548/491 |
| 4,598,060 A | 7/1986 | Schoenthal et al. | |
| 4,603,119 A | 7/1986 | Karl et al. | |
| 4,668,496 A | 5/1987 | Korb et al. | |
| 4,892,972 A | 1/1990 | Schroeder et al. | |
| 4,954,469 A | 9/1990 | Robinson | |
| 4,987,116 A | 1/1991 | Karl et al. | |
| 5,166,437 A | 11/1992 | Kairisalo et al. | |
| 5,362,908 A | 11/1994 | Schroeder et al. | |
| RE34,910 E | 4/1995 | Funkenbusch et al. | |
| 5,432,284 A | 7/1995 | Dygos et al. | |
| 5,449,655 A | 9/1995 | Albers et al. | 502/185 |
| 5,514,658 A | 5/1996 | Santos Benito et al. | |
| 5,538,929 A * | 7/1996 | Sudhakar et al. | 502/180 |
| 5,616,792 A | 4/1997 | Bartos et al. | |
| 5,672,558 A | 9/1997 | White et al. | |
| 5,756,833 A | 5/1998 | Rosen et al. | |
| 5,856,473 A | 1/1999 | Shankar | |
| 5,972,525 A | 10/1999 | Mori et al. | |
| 5,977,409 A | 11/1999 | Erhardt | |
| 6,040,344 A | 3/2000 | Gao et al. | |
| 6,066,589 A | 5/2000 | Malentacchi et al. | 502/185 |
| 6,277,780 B1 * | 8/2001 | Beckler et al. | 502/180 |
| 6,706,658 B2 | 3/2004 | White | 502/182 |
| 6,720,283 B2 | 4/2004 | Ding et al. | 502/184 |
| 6,992,037 B2 * | 1/2006 | Chen et al. | 502/182 |

OTHER PUBLICATIONS

Seif, Louis S., et al. "Selective Hydrogenolysis of Benzyl and Carbonbenzyloxy Protecting Groups for Hydroxyl and Amino Functions," Catalysts of Organic Reactions, 1990 147-216.

Studer, Martin, et al. "Influence of Catalyst Type, Sovlent, Acid and Base on the Selectivity and Rate in the Catalytic Debenzylation of 4-chloro-N,N-dibenzyl aniline with Pd/C and H2," Journal of Molecular Catalysis A: Chemical 112 (1996) 437-445.

International Search Report mailed Feb. 21, 2003 related to PCT/US02/26880 filed Apr. 23, 2002.

E. Auer, et al.; "Carbons as Supports for Industrial Precious Metal Catalysts"; Applied Catalysis A: General 173 (1998) 259-271.

International Search Report for PCT/US06/21721 dated Oct. 25, 2006.

* cited by examiner

PRECIOUS METAL CATALYST FOR DEBENZYLATION

RELATED APPLICATIONS

This application is a continuation-in-part of U.S. patent application of Ser. No. 09/954,235 which was filed Sep. 17, 2001 now U.S. Pat. No. 6,992,037 entitled IMPROVED PRECIOUS METAL CATALYST FOR DEBENZYLATION, which is incorporated herein by reference.

FIELD OF THE INVENTION

The present invention generally relates to catalyst composites, methods of making and employing the catalyst composites, and methods of debenzylation. The present invention particularly relates to catalyst materials and methods associated with the deprotection of hydroxy and amino functional groups.

BACKGROUND

Catalytic processes are indispensable in the chemical industry. Frequently, catalytic processes employ a catalyst that is incorporated on a support. Effective use of the catalyst often corresponds to the quality of the catalyst support. Poor quality catalyst supports, due to at least one of poor structure, physical degradation, chemical degradation, undesirable properties, and inconsistent properties, limit the effectiveness of catalysts incorporated therein. Conditions such as high temperatures, high pressures, and high or low pH environments present challenges to the integrity of catalyst supports.

Palladium catalysts are employed in synthetic organic chemistry, particularly in the pharmaceutical industry, for debenzylation. Commercially available palladium debenzylation catalysts are made on a carbon support having a surface area below 1,000 $m^2/g$, wherein about 50% of the surface area is located in micro pores (below 20 Å). Such carbon supports also have a ratio of micro pore volume to total pore volume of 20% or more.

Non-carbon catalyst supports are employed in catalytic processes in attempts to overcome the disadvantages associated with conventional carbon supported catalysts. Non-carbon supports include alumina supports, silica supports, alumina-silica supports, various clay supports, titania, and zirconium supports. However, there are at least one of two disadvantages associated with non-carbon catalyst supports; namely, that they may loose physical strength, and that they are dissolved in corrosive environments (such as acidic solutions).

Debenzylation involves separating a benzyl group from a functional group. One attractive use for debenzylation is cleaving a benzyl protective group from an amino or hydroxy functional group during organic synthesis. For example, during the synthesis of a multifunctional organic compound, reactive sites must be temporarily blocked until completion of the compound. Otherwise, reactive sites such as amino or hydroxy functional groups undesirably participate in reactions designed to create the compound of interest. Benzyl groups are consequently often employed as protective groups to prevent unwanted reactions.

The effectiveness and usefulness of a given protective group is determined, in part, by the ease in which it can be attached and subsequently removed from the organic compound being synthesized. Using conventional palladium debenzylation catalysts, it is sometimes difficult to reach a sharp end point for deprotection using benzyl protective groups. As a result, synthetic organic chemists sometimes select non-catalytic techniques for deprotection.

The effectiveness and usefulness of a given protective group is also determined, in part, by the selectivity associated with deprotection (removal of the protective group from the compound of interest). There are two notable aspects to selectivity.

First, in some instances, the same protective group may be employed to protect two or more different functional groups. Selectivity thus refers to the ability to remove the protective group from one functional group without removing it from another, different functional group. For example in organic synthesis, it may be desirable to cleave a first benzyl protective group from an amino functional group while not cleaving a second benzyl protective group from a hydroxy functional group located at a different position on the compound of interest.

Second, selectivity may refer to the ability to remove the protective group from a functional group without causing any unwanted side reactions. In this connection, deprotection using palladium debenzylation catalysts involves hydrogenolysis of the benzyl protective group. However, hydrogenolysis may hydrogenate a number of functional groups that may be present in the organic compound of interest. Groups such as $C{=}C$, $C{\equiv}C$, $C{\equiv}N$, $-RNO_2$, -aryl-halogen, and the like can be hydrogenated under relatively mild conditions using palladium catalysts.

Finally, the effectiveness and usefulness of a given protective group is determined, in part, by cost considerations. Deprotection of amine groups often requires relatively large amounts of palladium catalyst. This coupled with the high cost of palladium metal, sometimes works to disfavor the use of palladium catalysts.

SUMMARY

The present invention provides catalyst composites and methods for improved debenzylation reactions. The catalyst support of the present invention has a certain total pore volume/micro pore volume and/or total pore surface area/micro pore surface area and/or a low phosphorus content that facilitates improved catalyst activity and/or selectivity. The catalyst composite of the present invention exhibits improved selectivity with regard to selected removal of a protective group from one functional group in favor over another functional group coupled to the same protective group. The catalyst composite of the present invention may exhibit improved selectivity by minimizing side reactions, such as mitigating hydrogenation of unsaturated carbon-carbon bonds and the like during debenzylation.

One aspect of the invention relates to catalyst composite containing a metal catalyst and a specifically defined carbon support containing a carbonaceous material. For example, the carbon support may have a total pore surface area of about 800 $m^2/g$ or more and about 2,000 $m^2/g$ or less where about 20% or less of the total pore surface area is micro pore surface area. In this embodiment, the carbon support may have a micro pore surface area of about 200 $m^2/g$ or less. In another aspect of the invention, the carbon support may have a total pore volume of at least about 0.75 cc/g where about 15% or less of the total pore volume is micro pore volume. In this embodiment, the carbon support may have a micro pore volume of about 0.1 cc/g or less. In yet another aspect of the invention, the carbon support may have a phosphorus content of about 0.75% by weight or less. In other aspects of the invention, a methods of making and using the catalyst composite are disclosed.

DETAILED DESCRIPTION

In one embodiment, the present invention involves the preparation of a catalyst composite containing a precious metal catalyst and a carbon support. The composite according to the present invention is prepared by mixing a carbon support containing a carbonaceous material with a precious metal compound, wherein the carbon support has a certain pore surface area and/or micro pore volume and/or low phosphorus content. Thus, in another embodiment, the present invention involves the preparation of a catalyst composite containing a carbon support and a precious metal catalyst. In yet another embodiment, the present invention involves the use of a catalyst composite in a catalytic hydrogenolysis process, such as in the debenzylation of benzyl protective groups.

The carbon support contains a carbonaceous material, and optionally one or more additives. The carbonaceous material may be obtained or derived from any suitable carbon source. The carbonaceous material initially used is an activated carbon, or a non-activated carbon that may be converted to activated carbon at some point during the formation of the carbon support. For example, charcoal (a non-activated carbonaceous material) may be converted to activated carbon during a heat treatment step (subsequently described). Carbonaceous materials include activated carbon derived from coal, lignite, wood, nutshells, peat, pitches, cokes, and the like; and non-activated carbon derived from carbon char powder (e.g. charcoal).

The carbonaceous material combined with any optional additives is typically in powder form. In other words, the carbonaceous materials are not extruded. When the carbonaceous materials are in powder form, use in slurry applications is facilitated. In one embodiment, the carbonaceous material has a particle size (average particle size) of less than about 100 microns. In another embodiment, the carbonaceous material has a particle size of less than about 80 microns. In yet another embodiment, the carbonaceous material has a particle size of less than about 50 microns. In still yet another embodiment, the carbonaceous material has a particle size of less than about 35 microns.

Carbonaceous materials are commercially available from a number of sources or they may be made. Carbonaceous materials are commercially available from Calgon, Ceca, Norit, and Westvaco. For example, carbonaceous materials may be derived from coal, coke, coal coke, petroleum coke, lignite, polymeric materials, graphite, bone, wood, nut shells including coconut shells, resin wastes, lignocellulosic materials including pulp and paper, kernel, fruit pits, and sugar. The source of carbonaceous materials is not critical to the present invention. U.S. Pat. Nos. 3,084,394; 3,109,712; 3,171,720; 3,198,714; 3,310,611; 3,387,940; 3,342,555; 3,345,440; 3,352,788; 3,446,593; 3,565,980; 3,574,548; 3,626,042; 3,628,984; 3,634,569; 3,635,676; 3,663,171; 3,859,421; 4,029,567; 4,082,694; 4,206,078; 4,263,268; 4,329,260; 4,603,119; 4,668,496; 4,954,469; 4,987,116; describe various carbonaceous materials and are hereby incorporated by reference in this regard.

The carbonaceous materials are chemically activated or non-chemically activated. The carbonaceous materials used to form the carbon support, and thus the carbon supports themselves, are either chemically activated or physically activated, although chemically activated carbonaceous materials are preferred. Chemical activating agents include one or more of alkali metal hydroxides, alkali metal carbonates, alkali metal sulfide, alkali metal sulfates, alkaline earth metal carbonates, alkaline earth metal chlorides, alkaline earth metal sulfates, alkaline earth metal phosphates, phosphoric acid, polyphosphoric acid, pyrophosphoric acid, zinc, chloride, sulfuric acid, and the like. Chemical activation is conducted by contacting one or more carbonaceous materials with one or more chemical activating agents, mixing, optionally heating, optionally washing/rinsing, and optionally drying the chemically activated material.

In one embodiment, the carbon support contains about 50% by weight or more and about 100% by weight or less of at least one carbonaceous material. In another embodiment, the carbon support contains about 60% by weight or more and about 99.9% by weight or less of at least one carbonaceous material.

The carbon support contains a relatively small amount of phosphorus. If necessary, the carbon support may be post treated to lower the phosphorus content. In one embodiment, the carbon support contains about 0.75% by weight or less of phosphorus, but at least some detectable amount of phosphorus such as about 0.0001% by weight or more of phosphorus. In another embodiment, the carbon support contains about 0.5% by weight or less of phosphorus, but at least some detectable amount of phosphorus such as about 0.001% by weight or more of phosphorus. In yet another embodiment, the carbon support contains about 0.4% by weight or less of phosphorus, but at least some detectable amount of phosphorus such as about 0.01% by weight or more of phosphorus.

Since conventional chemically activated carbon supports typically contain at least 1% by weight or more of phosphorus, the relatively low phosphorus content of the carbon supports described herein can be advantageous in some instances, especially the relatively low phosphorus content of the chemically activated carbon supports described herein. It has been found that relatively larger amounts of phosphorus (such as 1% by weight or more) in carbon supports inhibits the activity of precious metal catalysts, particularly palladium, compared to carbon supports containing about 0.75% by weight or less of phosphorus.

The carbon support may be made by mixing the carbonaceous material and any optional additives, forming the mixture into a shaped material, optionally drying the shaped material, either pulverizing the shaped material to provide the carbon support or heat treating the shaped material and then pulververizing to provide the carbon support. When mixing the carbonaceous material and any optional additives, it is preferable to add water (and/or other liquid solvent). Tap water or deionized water may be employed, but deionized water is preferred. Water is added to facilitate mixing and subsequent forming (for instance, extrusion), and thus it is added in any amount suitable to facilitate mixing and subsequent forming. Since water is eventually removed in subsequent drying and heat treatment steps, the amount of water added is not critical to the present invention.

Nevertheless, in one embodiment, the mixture of optional additives and carbonaceous material typically contains from about 5% to about 80% by weight water. In another embodiment, the mixture of optional additives and carbonaceous material contains from about 10% to about 70% by weight water. In another embodiment, the mixture of optional additives and carbonaceous material contains from about 20% to about 60% by weight water.

Additives include any material that facilitates mixing and subsequent forming. Additives include rheology control agents, extrusion aids, suspension agents, surfactants, low boiling organic compounds, rosin materials, polymeric additives, and dispersing agents such as ammonium lignosulfonates. Rheology control agents include cellulose ethers, polyvinyl alcohols, and polyalkylene oxides. Examples of cellulose ethers include sodium carboxymethylcellulose (CMC), hydroxyethylcellulose (HEC), methylcellulose (MC) and derivatives thereof. One commercially available cellulose ether is Methocel. Methocel, which contains water and hydroxypropylmethylcellulose ether polymer, has a high thermal gelatin point, such as the products designated as K4M and K15M available from Dow Chemical Company. Preferred polyalkylene oxides include polyethylene oxides. Extrusion aids include glycol compounds, such as polyalkylene glycols. In a specific embodiment, polyethylene glycol, such as PEG 400 available from Union Carbide can be added as an extrusion aid. Generally, the glycol compounds are dissolved in water and then added to the dry ingredients.

In one embodiment, the carbon support typically contains from about 0.01% to about 10% by weight of at least one additive. In another embodiment, the carbon support contains from about 0.1% to about 5% by weight of at least one additive.

The mixture of carbonaceous powder and any optional ingredients may be mixed well in a high shear mixer with water and a rheology control agent, such as Methocel until a rather stiff dough is obtained. This dough can be extruded or formed into any suitable shape including cylinders, cubes, stars, tri-lobes, quadra-lobes, pellets, spheres by suitable mechanical means. In a preferred embodiment, mixing is conducted in a high intensity environment, such as that supplied by a Littleford Mixer available from Littleford Day, Inc., Florence, Ky. Mixing is conducted for a time sufficient so that a fine uniform mix results. In one embodiment, deionized water is added to the mixture during mixing in an amount to yield a stiff, dough-like material suitable for extrusion.

In one embodiment, the mixture of carbonaceous material and optional additives is mixed in a high intensity mixer from about 5 minutes to about 100 minutes. In another embodiment, mixture of carbonaceous material and optional additives is mixed in a high intensity mixer from about 10 minutes to about 60 minutes.

After mixing, the mixed material is formed into a suitable shape, then pulverized. Examples of extrusion machines include extrusion molding machines, single screw extruders, twin screw extruders, coextruders, pin extruders, linear extruders, and monofilament extruders.

The extruded material has its components (the carbonaceous material and any optional additives) uniformly mixed therein. Uniformly mixed optional additives and carbonaceous material in the subsequent resultant catalyst support contributes to the advantageous properties of the resultant extruded catalyst support and resultant catalyst composite containing the catalyst support.

After forming the material, before or after pulverizing, the formed material is optionally dried to remove any remaining liquid (and typically to remove remaining water). Drying is conducted in at least one of a desiccator, under a vacuum (reduced pressure), and/or elevated temperature (baking) for a sufficient period of time to remove any remaining liquid from the formed material. Drying the formed material contributes to the attrition resistance properties of the resultant carbon support.

The manner in which the carbon material is dried is not critical, but in many instances the drying conditions primarily depend upon at least one of the dimensions of the carbon material and the shape of the carbon material. In one embodiment, the dried carbon material contains less than about 3% by weight free moisture. In another embodiment, the dried carbon material contains less than about 1% by weight free moisture. In yet another embodiment, the dried carbon material contains less than about 0.5% by weight free moisture.

In one embodiment, drying involves at least one of maintaining an elevated temperature (above about 35° C.) overnight, desiccation overnight, and under a vacuum overnight. When employing elevated temperatures, in one embodiment, the carbon material is heated from about 35° C. to about 150° C. for a time from about 5 seconds to about 6 hours. In another embodiment, the carbon material is heated from about 40° C. to about 110° C. for a time from about 30 seconds to about 30 minutes.

After drying, the carbon material is optionally heat treated. However, in one embodiment, the drying step may be incorporated into the heat treatment step by starting the heat treatment at a relatively low temperature (low temperatures relative to the heat treatment temperatures). The dried material is heat treated in any suitable manner to provide a catalyst support and to provide a catalyst support containing a carbonaceous material having properties corresponding with those of activated carbon (especially in embodiments where a nonactivated carbonaceous material is employed).

In one embodiment, heat treatment involves heating the carbon material at a temperature from about 600° C. to about 1,500° C. In another embodiment, heat treatment involves heating the carbon material at a temperature from about 700° C. to about 1,000° C. It is noted that the temperature may vary within a temperature range. For example, the temperature may be ramped or steadily increased during the length of the heat treatment.

The length of time the carbon material is optionally heated primarily depends upon the temperature, the contents of atmosphere, the related equipment, and the identity of the components (the specific type of carbonaceous material and the optional additives). In one embodiment, heat treatment involves heating the carbon material from about 15 minutes to about 5 hours. In another embodiment, heat treatment involves heating the carbon material from about 30 minutes to about 4 hours. Heating time refers to the amount of time that the carbon material itself is at the temperature specified (and thus does not include ramping up or cooling down).

In one embodiment, the atmosphere in which the optional heat treatment is conducted contains at least steam or water vapor. The atmosphere may further contain at least one of an inert gas, air, oxygen, and carbon dioxide. Inert gases include the noble gases and nitrogen. Noble gases include helium, neon, argon, krypton, and xenon. In another embodiment, the atmosphere in which the heat treatment is conducted contains at least one of steam/water vapor and an inert gas. In this connection, in one embodiment, the heat treatment atmosphere contains a substantially inert atmosphere, such as from about 50% to about 100% of at least one an inert gas and from about 0% to less than about 50% of one or more of steam, air, oxygen, and carbon dioxide.

The resultant carbon supports of the present invention possess a high degree of hardness, and consequently, they tend to resist breaking, chipping, cracking and other physical damage. The resultant carbon supports are characterized as having uniformly sized and shaped particles. The resultant carbon supports are basic in that they are not acidic nor neutral. Another advantage associated with resultant carbon supports of the present invention is that the level of porosity and/or extent of surface area are controllable, primarily by varying the heat treatment parameters and by varying the relative amounts of the ingredients (the carbonaceous material and the optional additives). Porosity and/or surface area may also be controllable or is further controllable by the amount and the type of additive, such as the rheology control agent or the extrusion aid. The resultant carbon supports of the present invention may also possess a relatively small amount of phosphorus compared to conventional carbon catalyst supports.

The resultant carbon supports are basic in that when contacted with water, a basic reaction occurs and the carbon-water slurry has a pH of at least about 8. Thus, the resultant carbon support is inherently a base. In another embodiment, when the resultant carbon support is contacted with water, the pH is at least about 8.5. In yet another embodiment, when the resultant carbon support is contacted with water, the pH is at least about 9. The term basic carbon support therefore refers to a carbon support that when placed in water, yields a pH of at least about 8, at least about 8.5, or at least about 9. While not wishing to be bound by any theory, it is believed that the basic nature of the resultant carbon supports contributes to or improves at least one of: facilitates precious metal impregnation, facilitates a debenzylation reaction, facilitates formation of desirable porosity and/or pore sizes.

Generally, the total pore surface area of the carbon supports of the present invention correspond to a weighted average of the total surface pore area of the optional additives and carbonaceous material. In one embodiment, the total pore surface area of the carbon supports is about 800 $m^2/g$ or more and about 2,000 $m^2/g$ or less. In another embodiment, the total pore surface area of the carbon supports is about 1,000 $m^2/g$ or more and about 1,900 $m^2/g$ or less.

The carbon supports generally have a unique distribution of micro pore surface area that contributes, in part, to the advantages obtained by the present invention. While not wishing to be bound by any theory, it is believed that the distribution of micro pore surface area in the carbon supports of the present invention leads to improved activity for the catalyst composite. Mirco pore surface area is that surface area of the carbon support located in pores having a diameter of 20 Å or less. In one embodiment, the micro pore surface area of the carbon supports is about 200 $m^2/g$ or less. In another embodiment, the micro pore surface area of the carbon supports is about 150 $m^2/g$ or less. In yet another embodiment, the micro pore surface area of the carbon supports is about 100 $m^2/g$ or less.

In one embodiment, the percentage of the total pore surface area of the carbon supports of the present invention that is micro pore surface area is about 20% or less. In conventional carbon supports, typically about 50% of the total pore surface area is due to micro pore surface area. In another embodiment, the percentage of micro pore surface area of the total pore surface area of the carbon supports is about 15% or less. In yet another embodiment, the percentage of micro pore surface area of the total pore surface area of the carbon supports is about 10% or less. In still yet another embodiment, the percentage of micro pore surface area of the total pore surface area of the carbon supports is about 8% or less.

The carbon supports generally have a unique distribution of pore volume that contributes, in part, to the advantages obtained by the present invention. While not wishing to be bound by any theory, it is believed that the distribution of pore volume in the carbon supports of the present invention leads to improved activity for the catalyst composite.

In one embodiment, the carbon support of the present invention has a total pore volume of at least about 0.75 cc/g. In another embodiment, the carbon support has a total pore volume of at least about 1 cc/g. In yet another embodiment, the carbon support has a total pore volume of at least about 1.1 cc/g.

In one embodiment, the carbon support of the present invention has a micro pore volume of about 0.1 cc/g or less. Micro pore volume is the pore volume in pores having a diameter of 20 Å or less. In another embodiment, the carbon support has a micro pore volume of about 0.075 cc/g or less. In yet another embodiment, the carbon support has a micro pore volume of about 0.05 cc/g or less. In still yet another embodiment, the carbon support has a micro pore volume of about 0.03 cc/g or less.

In the carbon supports of the present invention, in one embodiment, the percentage of total pore volume that is micro pore volume is about 15% or less. In conventional carbon supports, typically about 25% of the total pore volume is micro pore volume. In another embodiment, the percentage of total pore volume that is micro pore volume is about 10% or less. In yet another embodiment, the percentage of total pore volume that is micro pore volume is about 5% or less.

Pore volume may be determined by a nitrogen absorption test, such as using a in accordance with the analysis method outlined in ASTM D 4641-88 entitled "Standard practice for calculation of pore size distributions of catalysts from nitrogen absorption isotherms" which is incorporated by reference herein.

In one embodiment, the present invention involves forming a catalytic composite by impregnating the carbon support with a solution of at least one catalytically active metal. The impregnation is effected by treating the carbon support with an aqueous or organic solution of the desired metal or combination of metals in an amount sufficient to deposit at least one catalytically active metal on or near the surface of the support, thereby providing a catalyst composite. The carbon support/carbonaceous material may be formed, extruded, or powdered; processed or unprocessed.

Catalytically active metals typically include precious metals. Examples of catalytically active metals and mixture of metals include palladium, palladium hydroxide, palladium and rhenium, palladium and rhodium, palladium and tungsten, palladium and nickel, palladium and tin, palladium and copper, palladium and ruthenium, palladium and lead, palladium and germanium, palladium and platinum, platinum, platinum and rhenium, platinum and ruthenium, platinum and tungsten, platinum and nickel, platinum and tin, platinum and iron, platinum and copper, platinum and rhodium, platinum and lead, platinum and germanium, cobalt, rhodium, nickel, ruthenium, osmium, iridium, various combinations thereof, etc. Palladium and platinum catalysts include palladium with about 10% by weight or less platinum as a promoter as well as platinum with about 10% by weight or less palladium as a promoter. It is to be understood that the aforementioned list of catalytically active metals are only representative, and thus not limiting of the type of metals which may be impregnated on the carbon support surface.

The catalyst may be impregnated onto/into the carbon support in any suitable manner. For example, immersion techniques, spraying techniques, and incipient wetness techniques may be employed. Generally, a slurry is formed containing the carbon support and the metal catalyst (or a compound containing some form of the metal catalyst such as a metal salt), the carbon support and the metal catalyst come into contact with each other, and the slurry is filtered to provide a catalyst composite. The carbon support and the metal catalyst are contacted with each other at a temperature of about 2° C. or more and about 100° C. or less. In another embodiment, the carbon support and the metal catalyst are contacted with each other at a temperature of about 5° C. or more and about 70° C. or less. The slurry may be heated prior to filtering. In one embodiment, the slurry is heated to about 40° C. or more and about 100° C. or less. In another embodiment, the slurry is heated to about 50° C. or more and about 90° C. or less.

In one embodiment, the amount of catalyst in the catalyst composite is from about 0.1% to about 30% by weight. In another embodiment, the amount of catalyst in the catalyst composite is from about 0.25% to about 20% by weight. In yet another embodiment, the amount of catalyst in the catalyst composite is from about 0.5% to about 10% by weight. In one embodiment, the amount of the carbon support in the catalyst composite is from about 70% to about 99.9% by weight. In another embodiment, the amount of the carbon support in the catalyst composite is from about 80% to about 99.75% by weight. In yet another embodiment, the amount of the carbon support in the catalyst composite is from about 90% to about 99.5% by weight.

The catalyst composites of the present invention are suitable for use in catalytic processes. Catalytic processes where the catalyst composites of the present invention can be employed include hydrogenation, hydrogenolysis, rearrangement, dehalogenation, isomerisations, Rosemund reactions, hydrogen transfer reactions, high pressure reactions, deprotection, and debenzylation, such as O-debenzylation and N-debenzylation. Hydrogenolysis may be employed for benzyl acohols, benzyl ethers, benzyl acetals cyclic acetals, and N-debenzylation.

These catalytic processes are generally know to those skilled in the art. They are described in U.S. Pat. Nos. 6,040, 344; 5,977,409; 5,856,473; 5,514,658; 5,432,284; 5,166,437; 4,595,765; 4,500,541; 4,431,820; Org. Reactions, 7,263 (1953); C. Murchu, Tetrahedron Lett., 38, 3231 (1969); W. M. Pearlman, Tetrahedron Lett., 1663 (1967); H. Dahn, et al, Helv. Chim. Acta., 53, 1370 (1970); Y. Sugi and S. Mitsui, Tetrahedron, 29, 2041 (1973); A. Kieboom and F. Van Rantwijk Eds. Hydrogenation And Hydrogenolysis In Synthetic Organic Chemistry, Delft University Press, Netherlands, 132 (1977); Y. Sugi and S. Mitsui, Tetrahedron, 29, 2041 (1973); R. Baltzly and P. Russell, J. Am. Chem. Soc., 75, 5598 (1953); A. Kieboom, et al., Journal of Catalysis, 20, 58 (1971); M. Freifelder, Practical Catalytic Hydrogenation, John Wiley & Sons (1971); Bernotas and Cube, Synthetic Communications, 20(8), 1209-1212 (1990); Studer and Blaser, J. of Molecular Catalysis A: Chemical 112 (1996) 437-445; Catalysts of Organic Reactions, Eds. Blake and Blackburn, Marcel-Dekker, Inc., New York, 1990, p. 197-216; and A. Bellamy, Tetrahedron, 16, 4711 (1995) which hereby incorporated by reference in this regard.

The catalyst composites of the present invention are suitable for use in selective debenzylation, such as debenzylating a protected functional nitrogen atom without debenzylating a protected functional oxygen atom on the same molecule. Selective debenzylation is improved using the catalyst composites of the present invention since selectivity can be increased.

Protective groups temporarily bonded to functional atoms in an organic compound often include benzyl and carbobenzyloxy groups. These protective groups are removed or cleaved from the organic compound by catalytic debenzylation. The organic compound is often a pharmaceutical compound, or intermediate thereof, a pesticide, or intermediate thereof, a herbicide, or intermediate thereof, an amino acid or peptide, or intermediate thereof, a heterocyclic compound, or intermediate thereof, a carbohydrate, or intermediate thereof, a steroid, or intermediate thereof, and the like. Synthesizing or processing one or more of the pharmaceutical compound, pesticide, amino acid or peptide, heterocyclic compound, and steroid typically requires the use of a protective group. Sharp endpoints to deprotection reactions lead to improved yields of the one or more of the pharmaceutical compound, pesticide, amino acid or peptide, heterocyclic compound, and steroid.

The specific catalytic reactions/processes are too numerous to list, but the following are specific examples. Catalytic debenzylation involves the following general reaction:

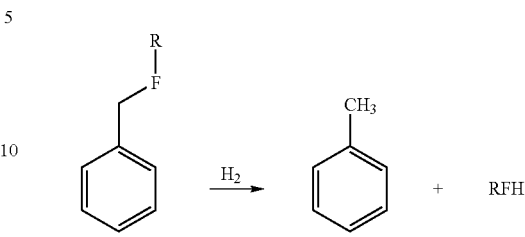

where R is an organic structure and F is a functional atom or group. Functional atoms include oxygen (corresponding to a hydroxy group), sulfur (corresponding to a thiol group), and nitrogen (corresponding to an amino group).

Generally, debenzylation is conducted under acidic conditions using polar solvents, low pressure and relatively high temperature. Typical debenzylation reactions are carried out at a temperature from about 5° C. to about 100° C. with about 1 to about 10 atmospheres of hydrogen pressure in an alcohol and/or an acid solvent.

In one embodiment, the catalyst composites of the present invention have about 25% or more higher reaction rates than conventional catalyst composites containing the same amount of precious metal catalyst. In another embodiment, the catalyst composites of the present invention have about 30% or more higher reaction rates than conventional catalyst composites containing the same amount of precious metal catalyst.

The following examples demonstrate this advantage. The following examples also illustrate the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

A catalyst composite containing 3% by weight palladium and 97% by weight carbon powder is prepared. Sodium carbonate is dissolved in deionized water, to which is added 47 g carbon powder having a total surface area of 1,600 m$^2$/g, a micro surface area of 96 m$^2$/g, 6% of the total surface area is attributable to micro surface area, a total pore volume 1.2 cc/g, a micro pore volume of 0.027 cc/g, 2.3% of the total pore volume is attributable to micro pore volume to form a slurry. Dissolved sodium carbonate solution is added to a sodium palladium chloride solution (20% w/w Pd) until the pH is approximately 8. 7.47 g of the palladium solution is added to the carbon powder slurry and mixed. The combined solution is then filtered and washed.

EXAMPLE 2

A catalyst composite containing 5% by weight palladium and 95% by weight carbon powder is prepared. Sodium carbonate is dissolved in deionized water, to which is added 47 g carbon powder having a total surface area of 1,600 m$^2$/g, a micro surface area of 96 m$^2$/g, 6% of the total surface area is attributable to micro surface area, a total pore volume 1.2 cc/g, a micro pore volume of 0.027 cc/g, 2.3% of the total pore volume is attributable to micro pore volume to form a slurry.

Dissolved sodium carbonate solution is added to a sodium palladium chloride solution (20% w/w Pd) until the pH is approximately 8. 12.45 g of the palladium solution is added to the carbon powder slurry and mixed. The combined solution is then filtered and washed.

EXAMPLE 3

A catalyst composite containing 3% by weight palladium, 0.3% by weight platinum, and 96.7% by weight carbon powder is prepared. 48.44 g carbon powder having a total surface area of 1,600 m$^2$/g, a micro surface area of 96 m$^2$/g, 6% of the total surface area is attributable to micro surface area, a total pore volume 1.2 cc/g, a micro pore volume of 0.027 cc/g, 2.3% of the total pore volume is attributable to micro pore volume is added to deionized water to form a slurry, adjust pH to about 8 with 10% sodium carbonate solution. Mix 3.9 g of 3.99% sodium platinum chloride solution with 7.74 g 20% sodium palladium chloride solution, adjust pH to about 4 with 10% sodium carbonate solution. Add and mix the palladium-platinum solution to the carbon powder slurry, adjust the pH to about 9 with 10% sodium hydroxide solution. The combined solution is then filtered and washed.

COMPARATIVE EXAMPLE 1

A catalyst composite containing 5% by weight palladium and 95% by weight carbon powder is prepared. Sodium carbonate is dissolved in deionized water, to which is added 47 g carbon powder having a total surface area of 896 m$^2$/g, a micro surface area of 459 m$^2$/g, 51.2% of the total surface area is attributable to micro surface area, a total pore volume 0.75 cc/g, a micro pore volume of 0.217 cc/g, 28.9% of the total pore volume is attributable to micro pore volume to form a slurry. Dissolved sodium carbonate solution is added to a sodium palladium chloride solution (20% w/w Pd) until the pH is approximately 8. 12.45 g of the palladium solution is added to the carbon powder slurry and mixed. The combined solution is then filtered and washed.

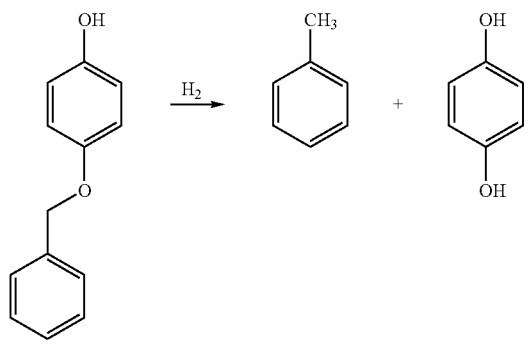

The catalyst composites of Examples 1 to 3 and Comparative Example 1 are employed to catalyze the following reaction.

The reaction involves the debenzylation of hydroquinone mono-benzyl ether. Table 1 reports the reaction rate constants for the reaction.

TABLE 1

| Example | % Pd | zero order rate constant moles/min-g cat. × 100 | moles/min-g Pd × 100 |
|---|---|---|---|
| 1 | 3 | 0.65 | 21.71 |
| 2 | 5 | 1.14 | 22.88 |
| 3 | 3 | 0.81 | 27.2 |
| CE1 | 5 | 0.62 | 12.39 |

The catalyst composites according to the invention, Examples 1 to 3, provide increased activity compared to conventional catalyst composites. The zero order rate constants are calculated as follows: catalyst weight basis (moles/min-g cat)

$$=60/(T_{0.5}-T_{0.25})/(0.1*\% \ cat \ \text{loading})/22.414*100$$

and Pd metal weight basis (moles/min-g Pd)

$$=60/(T_{0.5}-T_{0.25})/(0.1*\% \ cat \ \text{loading})/(\% \ \text{Pd in} \ cat*22.414)*100$$

wherein $T_{0.5}$ is the time to 0.5 liter hydrogen uptake and $T_{0.25}$ is the time to 0.25 liter hydrogen uptake (assuming a zero order reaction).

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A catalyst composite comprising:
   a basic carbon support comprising a carbonaceous material and about 0.75% by weight or less and about 0.0001% by weight or more of phosphorus, wherein the carbon support has a total pore surface area of about 1,000 m.sup.2/g or more and about 2,000 m$^2$/g or less, a micro pore surface area of about 100 m$^2$/g or less, about 8% or less of the total pore surface area is micro pore surface area, a total pore volume of at least about 1.1 cc/g, a micro pore volume of about 0.03 cc/g or less, and about 5% or less of the total pore volume is micro pore volume; and
   a precious metal catalyst.

2. The catalyst composite of claim 1, the basic carbon support yielding a pH of at least about 8.5 when placed in water.

3. The catalyst composite of claim 1, the basic carbon support comprising a carbonaceous material and about 0.5% by weight or less and about 0.001% by weight or more of phosphorus.

4. The catalyst composite of claim 1, the carbonaceous material comprises a chemically activated carbonaceous material.

5. The catalyst composite according to claim 1, wherein the catalyst composite comprises from about 70% to about 99.9% by weight of the basic carbon support and from about 0.1% to about 30% by weight of the precious metal catalyst.

6. The catalyst composite according to claim 1, wherein the precious metal catalyst comprises at least one selected from the group of palladium, palladium hydroxide, palladium and rhenium, palladium and rhodium, palladium and tungsten, palladium and nickel, palladium and tin, palladium and copper, palladium and ruthenium, palladium and lead, palladium and germanium, palladium and platinum, platinum, platinum and rhenium, platinum and ruthenium, platinum and tungsten, platinum and nickel, platinum and tin, platinum and iron, platinum and copper, platinum and rhodium, platinum and lead, platinum and germanium, cobalt, rhodium, nickel, ruthenium, osmium, and iridium.

7. The catalyst composite according to claim 1, wherein the basic carbon support yielding a pH of at least about 9 when placed in water.

8. The catalyst composite according to claim 1, wherein the precious metal catalyst comprises palladium.

9. The catalyst composite of claim 1 wherein the precious metal catalyst comprises palladium and the catalyst composite is a debenzylation catalyst.

10. A method of making a catalyst composite comprising:
providing a basic carbon support comprising a basic carbonaceous material, the basic carbon support having
a total pore surface area of about 1,000 $m^2$/g or more and about 2,000 m.sup.2/g or less, a micro pore surface area of about 100 $m^2$/g or less, about 8% or less of the total pore surface area is micro pore surface area;
a total pore volume of at least about 1.1 cc/g, a micro pore volume of about 0.03 cc/g or less, and about 5% or less of the total pore volume is micro pore volume;
a phosphorus content of about 0.75% by weight or less and about 0.0001% by weight or more; and
the basic carbon support yielding a pH of at least about 8 when placed in water; and
contacting a precious metal catalyst with the basic catalyst support to provide the catalyst composite.

11. The method according to claim 10, wherein the basic carbon support yielding a pH of at least about 8.5 when placed in water and the basic carbon support comprising about 0.5% by weight or less and about 0.001% by weight or more of phosphorus.

12. The method according to claim 10, wherein the precious metal catalyst is contacted with the basic catalyst support in a solution at a temperature of about 5° C. or more and about 100° C. or less.

13. The method according to claim 10, wherein the catalyst composite comprises from about 70% to about 99.9% by weight of the basic carbon support and from about 0.1% to about 30% by weight of the precious metal catalyst.

14. The method according to claim 10, wherein the precious metal catalyst comprises at least one selected from the group of palladium, palladium hydroxide, palladium and rhenium, palladium and rhodium, palladium and tungsten, palladium and nickel, palladium and tin, palladium and copper, palladium and ruthenium, palladium and lead, palladium and germanium, palladium and platinum, platinum, platinum and rhenium, platinum and ruthenium, platinum and tungsten, platinum and nickel, platinum and tin, platinum and iron, platinum and copper, platinum and rhodium, platinum and lead, platinum and germanium, cobalt, rhodium, nickel, ruthenium, osmium, and iridium.

15. A method of catalytically deprotecting an organic compound having a protected functional group, comprising:
contacting the protected organic compound with hydrogen and a catalyst composite comprising a precious metal catalyst and a basic carbon support comprising a basic carbonaceous material, the carbon support having
a total pore surface area of about 1,000 $m^2$/g or more and about 2,000 $m^2$/g or less, a micro pore surface area of about 100 $m^2$/g or less, about 8% or less of the total pore surface area is micro pore surface area;
a total pore volume of at least about 1.1 cc/g, a micro pore volume of about 0.03 cc/g or less, and about 5% or less of the total pore volume is micro pore volume;
a phosphorus content of about 0.75% by weight or less and about 0.0001% by weight or more; and
the basic carbon support yielding a pH of at least about 8 when placed in water; and
recovering an organic compound having an unprotected functional group.

16. The method according to claim 15, wherein contacting the protected organic compound with hydrogen and a catalyst composite is conducted at a temperature from about 2° C. to about 100° C. with about 1 to about 10 atmospheres of hydrogen pressure in a liquid comprising an alcohol.

17. The method according to claim 15, wherein the unprotected functional group is one of a hydroxy group and an amino group.

18. The method according to claim 15, wherein the organic compound having at least one unprotected functional group is one or more of a pharmaceutical compound, a pesticide, a herbicide, an amino acid, a peptide, a heterocyclic compound, a carbohydrate, and a steroid.

19. The method according to claim 15, wherein the organic compound having a protected functional group comprises a protective group selected from the group consisting of benzyl group and carbobenzyloxy group.

20. The method according to claim 15, wherein the organic compound having a protected functional group comprises two protected functional groups, a first functional group is a hydroxy group and a second functional group is an amino group.

* * * * *